US010524731B2

(12) United States Patent
Schweitzer et al.

(10) Patent No.: US 10,524,731 B2
(45) Date of Patent: Jan. 7, 2020

(54) ELECTRODE CONTACT FEEDBACK SYSTEM

(71) Applicant: St. Jude Medical, Atrial Fibrillation Division, Inc., St. Paul, MN (US)

(72) Inventors: Jeffrey A. Schweitzer, St. Paul, MN (US); Steven C. Christian, New Brighton, MN (US); Anthony D. Hill, Minneapolis, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 54 days.

(21) Appl. No.: 15/283,430

(22) Filed: Oct. 2, 2016

(65) Prior Publication Data

US 2017/0086750 A1 Mar. 30, 2017

Related U.S. Application Data

(63) Continuation of application No. 14/216,908, filed on Mar. 17, 2014, now Pat. No. 9,456,786.

(Continued)

(51) Int. Cl.
*A61B 5/1459* (2006.01)
*A61B 5/00* (2006.01)
*A61B 5/0408* (2006.01)
*A61B 5/042* (2006.01)
*A61B 18/14* (2006.01)
(Continued)

(52) U.S. Cl.
CPC ............ *A61B 5/6885* (2013.01); *A61B 5/042* (2013.01); *A61B 5/0408* (2013.01); *A61B 5/6852* (2013.01); *A61B 5/6886* (2013.01); *A61B 18/1492* (2013.01); *A61B 90/06* (2016.02); *A61B 2018/0019* (2013.01); *A61B 2018/0088* (2013.01); *A61B 2018/00297* (2013.01); *A61B 2018/00303* (2013.01); *A61B 2018/00351* (2013.01); *A61B 2090/065* (2016.02)

(58) Field of Classification Search
CPC ........ A61B 18/1492; A61B 2018/0019; A61B 2018/00297; A61B 2018/00351; A61B 2018/0088; A61B 2019/465; A61B 5/0408; A61B 5/042; A61B 5/6885; A61B 5/6886
See application file for complete search history.

(56) References Cited

U.S. PATENT DOCUMENTS 5,911,694 A 6/1999 Ikeda et al.
6,315,774 B1 * 11/2001 Daniel .................. A61B 18/24
600/104
(Continued)

FOREIGN PATENT DOCUMENTS

| CN | 103826561 | 5/2014 |
|---|---|---|
| EP | 2138123 | 12/2009 |
| EP | 2742886 | 6/2014 |

*Primary Examiner* — Mark D Remaly
(74) *Attorney, Agent, or Firm* — Dykema Gossett PLLC

(57) ABSTRACT

A sensing assembly for sensing contact with an object is disclosed. The contact sensing assembly may comprise an elongate tubular body. An electrode may be connected to the elongate tubular body. A vibration element is operatively connected with the electrode and configured to deliver a vibration-inducing signal to induce vibration of the electrode. A sensor is configured to monitor the electrode for a perturbation in the induced vibration. The perturbation results from contact between the electrode and the object.

19 Claims, 9 Drawing Sheets

Related U.S. Application Data

(60) Provisional application No. 61/798,138, filed on Mar. 15, 2013.

(51) Int. Cl.
*A61B 90/00* (2016.01)
*A61B 18/00* (2006.01)

(56) References Cited

U.S. PATENT DOCUMENTS

| | | | |
|---|---|---|---|
| 8,162,933 B2 | 4/2012 | Francischelli | |
| 2008/0275465 A1* | 11/2008 | Paul | A61B 18/1492 606/129 |
| 2009/0009657 A1* | 1/2009 | Kawai | H04N 5/23248 348/373 |
| 2009/0165318 A1 | 7/2009 | Weston | |
| 2009/0275827 A1 | 11/2009 | Aiken | |
| 2010/0145331 A1* | 6/2010 | Chrisitian | A61B 18/14 606/33 |
| 2011/0028812 A1* | 2/2011 | Benni | A61B 5/14553 600/323 |
| 2012/0065506 A1 | 3/2012 | Smith | |
| 2013/0116622 A1* | 5/2013 | Takagi | A61M 25/0084 604/131 |

* cited by examiner

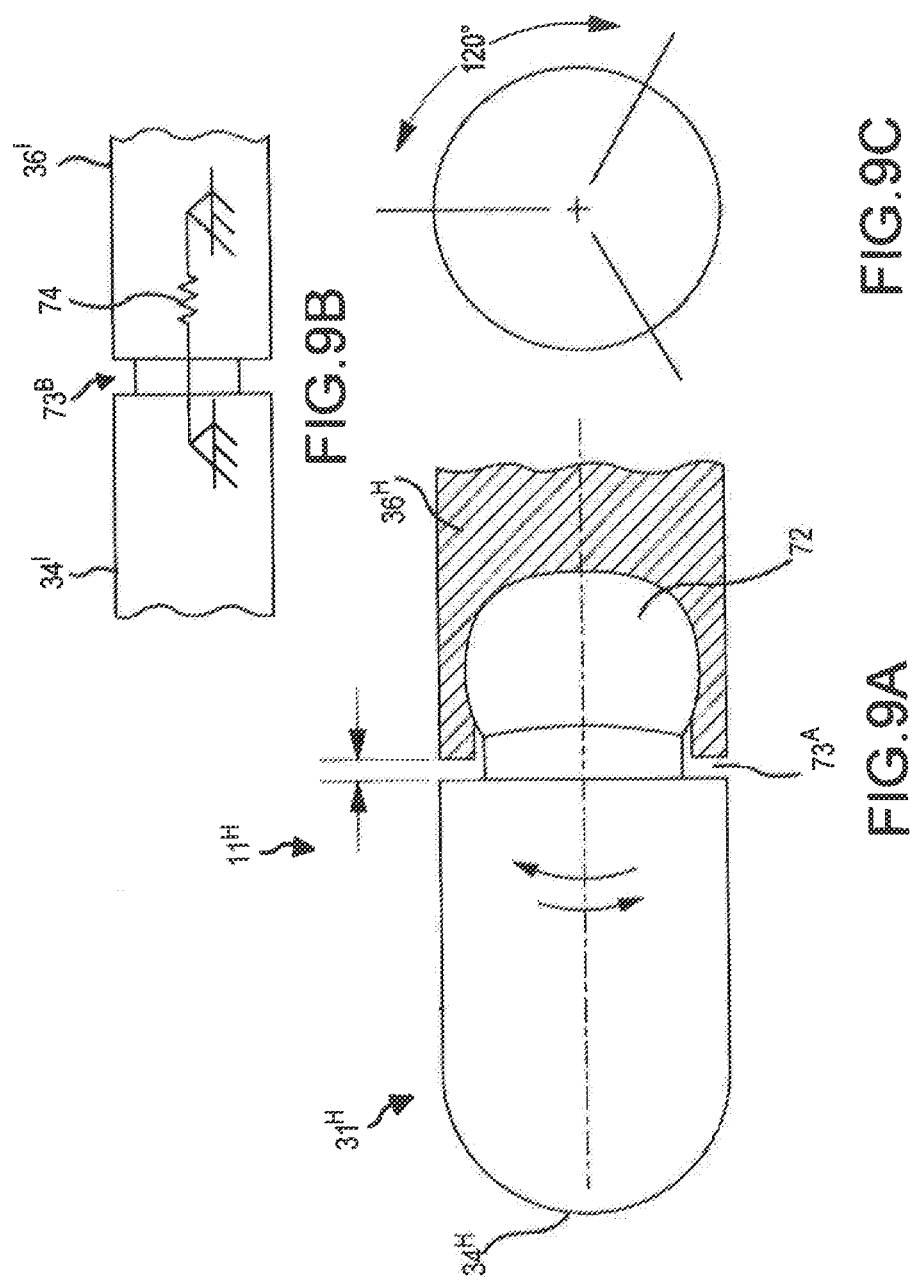

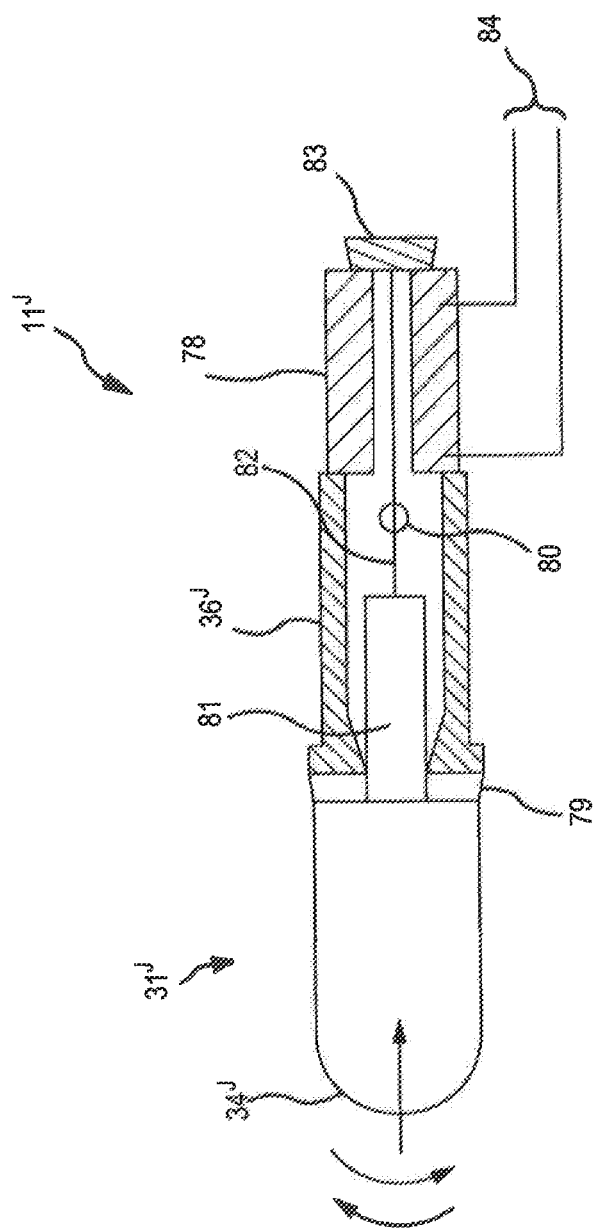

ELECTRODE CONTACT FEEDBACK SYSTEM

CROSS-REFERENCE TO RELATED APPLICATIONS

This application is a continuation of U.S. application Ser. No. 14/216,908, filed 17 Mar. 2014, which claims the benefit of U.S. provisional application No. 61/798,138, filed 15 Mar. 2013, both of which are hereby incorporated by reference as though fully set forth herein.

BACKGROUND a. Field of the Disclosure

This disclosure relates to medical devices, including a catheter configured to provide an indication of contact between the catheter and tissue in a body.

b. Background Art

Catheters are used to perform a variety of tasks within human bodies and other bodies including the delivery of medicine and fluids, the removal of bodily fluids, and the transport of surgical tools and instruments. In the diagnosis and treatment of atrial fibrillation, for example, electrodes may be added to catheters for electrophysiological mapping of the surface of the heart and to deliver ablative energy to the surface, among other tasks. Catheters are typically routed to a region of interest through the vascular system. In a conventional approach, an introducer is inserted through the skin surface and a sheath having an inner diameter greater than the outer diameter of the catheter is threaded through the vasculature to a region of interest. The catheter is then moved longitudinally through the sheath to the region of interest either manually or through the use of various types of robotic controls such as electromechanical drive systems.

In the case of an electrophysiological mapping catheter, electrode-to-issue contact facilitates meaningful electrograms and accurate mapping of the heart. In the case of ablation catheters, sufficient contact may be required for effective formation of ablative lesions in the tissue. A variety of mechanisms and techniques have been employed to determine contact between catheters and tissue, but these are either complex and require additional components that increase the cost, size, and complexity of the catheter, or they are nonspecific and difficult to interpret.

The disclosure herein has recognized a desire for a catheter that will minimize and/or eliminate one or more of the above-identified deficiencies.

BRIEF SUMMARY

The present invention generally relates to contact feedback mechanisms. Among other things, the present disclosure relates to contact feedback mechanisms used in conjunction with catheters during cardiac ablation or diagnostic procedures.

The disclosure is directed to contact feedback mechanisms, embodiments of which are described in detail herein that include systems providing angular displacement on a spherical joint between an electrode body and its mounting structure. In one embodiment, adjacent to the spherical joint are compliant members, such as silicone, that are compressed axially under load. The axial load creates a lateral or radial expansion of the compliant members. One or more of these compliant members are fitted with strain gauges or other sensor(s) that respond to the displacement of the material with a change in resistance. With appropriate electronics, this change in resistance can be used as a signal or output to control an audible, visual, tactile (e.g., vibratory), and/or other perceptible output system mounted in the catheter handle or displayed on a monitor or other display device.

Further, the output could be tuned to respond to the magnitude of the load applied to the electrode. For example, if the output is used to drive a handle-mounted transducer that vibrates with an input signal, a frequency, amplitude, phase, and/or magnitude of this output might change to represent the relative displacement or force applied to the electrode. Or, in a similar fashion, an LED mounted in the handle might change color or intensity as the electrode contact increases.

The disclosure further relates to contact feedback mechanisms in which the compliant members and strain gauges are replaced with piezoelectric transducers that are configured to respond to input forces from any electrode deflection. In addition, the input on the piezoelectric transducer can be amplified or concentrated with small evenly spaced risers on the interface between the electrode and transducer.

The disclosure further relates to a contact sensing assembly of a medical device that may comprise a catheter including an elongate tubular body having at least a distal end, an electrode, a transducer, and a sensor. The electrode may be connected to the elongate tubular body. The transducer may be driven by an electrical signal to vibrate the electrode at a defined frequency, such as a resonant frequency, which depends on the mechanical structure of the electrode. When the electrode contacts an object, the amplitude, phase, and/or frequency of the resonant vibrations of the electrode may be dampened, and the dampening may be sensed either through the electrical drive signal or through a second independent transducer located near the vibrating electrode.

The present disclosure further relates to a contact sensing assembly for a medical device that may comprise a catheter including an elongate body having a distal end, an electrode, an elastic or deformable member, and a sensor. The electrode may have an electrode tip and an electrode base. The electrode base may be connected to a distal end of the elongate body. The electrode tip may be connected to the electrode base via a spherical joint. The spherical joint may allow the electrode tip to move relative to the electrode base. The elastic or deformable member may be in contact with both the electrode tip and the electrode base and may be configured to elastically deform upon movement of said electrode tip relative to electrode base. The sensor may be located on the member. The sensor may be configured for measuring deformation of the member, where a magnitude of the measured deformation of the member may be correlated to a contact between the electrode tip and the object.

Additional embodiments are described and shown in detail herein. One mechanism to recognize tissue contact in this system is movement or displacement of the electrode relative to a catheter body interface. Upon such occurrence, an output signal can be generated to allow for audible, visual tactile, and/or other user feedback when a desired contact has been achieved between the electrode and the tissue, possibly above a predetermined threshold. This feedback, which may be varied, is provided through loads applied to sensors, including strain and pressure gauges, piezoelectric transducers, microelectromechanical systems (MEMS), optical or laser displacement transducers, linear voltage displacement transducers, microphones, among other devices.

The foregoing and other aspects, features, details, utilities, and advantages of the present invention will be apparent from reading the following description and claims, and from reviewing the accompanying drawings.

BRIEF DESCRIPTION OF THE DRAWINGS

FIGS. 6-9B are cross-sectional views of other embodiments of the electrode assembly of the medical device of FIG. 1 configured to use deflection sensing to sense contact.

FIG. 9C is an exemplary layout for transducers in the embodiment of the electrode assembly of the medical device of FIGS. 9A and 9B for deflection sensing.

FIGS. 10-12 are cross-sectional views of other embodiments of the electrode assembly of the medical device of FIG. 1 configured to use deflection sensing to sense contact.

DETAILED DESCRIPTION

Figure 1:
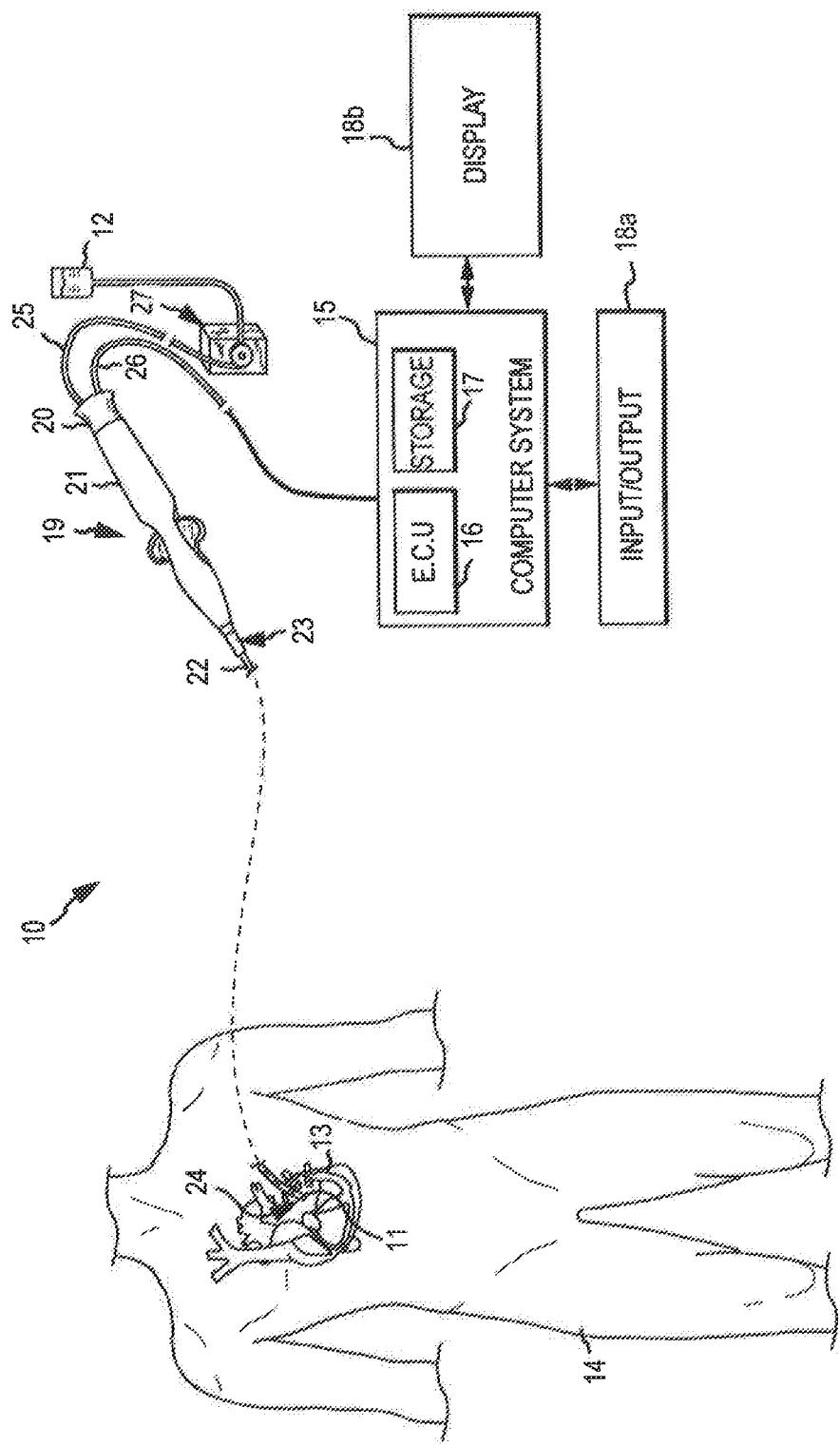
FIG. 1 is a schematic and block diagram view of a system incorporating an embodiment of a medical device having a contact sensing electrode assembly.

Referring now to the drawings wherein like reference numerals are used to identify identical components in the various views, FIG. 1 generally illustrates a system 10 having a catheter electrode assembly 11 configured to be used in the body for medical procedures. The electrode assembly 11 is included as part of a medical device such as a catheter 19 and may be used for diagnosis, visualization, and/or treatment of tissue 13 (such as cardiac or other tissue) in the body. For example, the electrode assembly 11 may be used for ablation therapy of tissue 13 or mapping purposes in a patient's body 14. FIG. 1 further shows various subsystems included in the overall system 10. The system 10 may include a main computer system 15 (including an electronic control unit 16 and data storage 17, e.g., memory). The computer system 15 may further include conventional interface components, such as various user input/output mechanisms 18a and a display 18b, among other components. Information provided by the electrode assembly 11 may be processed by the computer system 15 and may provide data to the clinician via the input/output mechanisms 18a and/or the display 18b, or in other ways as described herein.

In the illustrative embodiment, the catheter 19 may include a cable connector or interface 20, a handle 21, a tubular body or shaft 22 having a proximal end 23 and a distal end 24. The catheter 19 may also include other conventional components not illustrated herein such as a temperature sensor, additional electrodes, and corresponding conductors or leads. The connector 20 may provide mechanical, fluid and/or electrical connections for cables 25, 26 extending from a fluid reservoir 12 and a pump 27 and the computer system 15, respectively. The connector 20 may comprise conventional components known in the art and, as shown, may be disposed at the proximal end of the catheter 19.

The handle 21 provides a portion for a user to grasp or hold the catheter 19 and may further provide a mechanism for steering or guiding the shaft 22 within the patient's body 14. For example, the handle 21 may include a mechanism configured to change the tension on a pull-wire extending through the catheter 19 to the distal end 24 of the shaft 22 or some other mechanism to steer the shaft 22. The handle 21 may be conventional in the art, and it will be understood that the configuration of the handle 21 may vary. In an embodiment, the handle 21 may be configured to provide visual, auditory, tactile and/or other feedback to a user based on information received from the electrode assembly 11. For example, if contact to tissue 13 is made by the electrode assembly 11, the handle 21 may include light-emitting-diodes, a tone generator, a vibrating mechanical transducer, and/or other indicator(s), the outputs of which could vary in proportion to the signal sensed at the electrode assembly.

Figure 2:
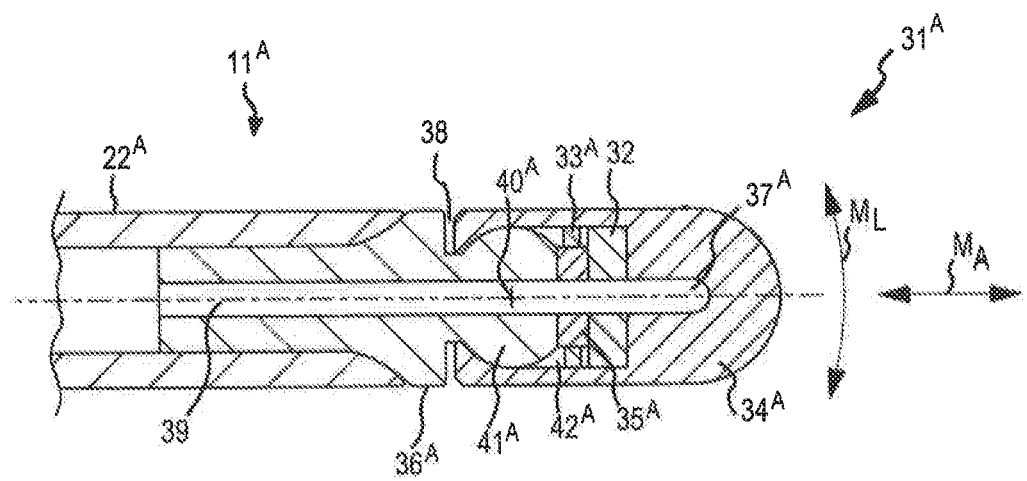
FIG. 2 is a cross-sectional view of an embodiment of the electrode assembly of the medical device of FIG. 1 configured to use vibration and deflection sensing to sense contact.

Referring to FIG. 2, a cross-sectional view of an embodiment of a distal portion of a catheter 19 having an electrode assembly $11^A$ is generally illustrated. The electrode assembly $11^A$ may be connected to the tubular body $22^A$ of the catheter 19 and located distal from an end of the tubular body $22^A$. The tubular body $22^A$ can be an elongate tubular body, in some examples. The electrode assembly $11^A$ may comprise an electrode $31^A$, a vibration element 32, a deformable member $35^A$, and a deflection measuring sensor $33^A$.

The electrode $31^A$ may include an electrode tip $34^A$ and an electrode base $36^A$, which can form a single, integral component. In some embodiments, the electrode tip $34^A$ may be configured to contact an object. The object can include, for example, tissue 13 of a patient. In some embodiments, the electrode tip $34^A$ can be configured to contact a medium. The medium can include, for example, blood of a patient or a saline solution. As used herein, the terms "object" and "medium" are meant to include both items in which the catheter tip may be immersed, as well as items against which the catheter tip may be touched and exert a force.

The vibration element 32 may be driven by an electrical signal to vibrate the electrode $31^A$ with a vibration inducing signal to induce vibration of the electrode $31^A$. The electrode $31^A$ can be vibrated by the vibration element 32 at a frequency, for example, a resonant frequency of the electrode tip $34^A$, which depends on the mechanical structure of the electrode $31^A$. The vibration element 32 can also be configured to vibrate the electrode $31^A$ at a particular amplitude and/or phase. In an example, the vibration element 32 can be a transducer that converts the electrical signal into mechanical energy (e.g., vibrations).

When the electrode tip $34^A$ comes into contact with the object and/or medium, the frequency, amplitude, and/or phase of the resonant vibration of the electrode tip $34^A$ may be changed (e.g., dampened). For example, prior to contact occurring between the electrode tip $34^A$ and the object and/or medium, the electrode assembly $11^A$ can vibrate at a particular frequency, amplitude, and/or phase. However, upon contact between the electrode tip $34^A$ and the object and/or medium, energy can be imparted from the electrode tip $34^A$ to the object in the form of vibrations, thus changing the particular frequency, amplitude and/or phase at which the electrode tip $34^A$ is vibrating. In addition, as a force between the object and the electrode tip $34^A$ is increased, more vibrations can be absorbed by the object, thus dampening vibration of the electrode and causing a perturbation. Increasing the force between the object and the electrode tip $34^A$ can place a larger surface area of the electrode tip $34^A$ in contact with the object, thus increasing an amount of vibrations that are absorbed by the object.

The perturbation (e.g., changed frequency, amplitude, phase at which the electrode tip $34^A$ is vibrating, electrical drive signal) may be sensed either through the electrical drive signal or through a second sensor (not shown) located near the vibrating electrode 31. The second sensor can be configured to monitor the electrode $31^A$ for a perturbation in the induced vibration of the electrode $31^A$. For example, the second sensor can be configured to sense a change in the frequency, amplitude, and/or phase at which the electrode tip $34^A$ is vibrating at before contact with the object and/or medium and after contact with the object and/or medium. In addition, upon contact of the electrode tip $34^A$ with the object and/or medium, the electrical drive signal may change. For example, upon contact of the electrode tip $34^A$ with the object and/or medium, a change in energy used to drive the electrode tip $34^A$ may occur, as a result of energy being imparted from the electrode tip $34^A$ to the object and/or medium. As such, the change in energy may be reflected by a change in current and/or voltage used to vibrate the electrode tip $34^A$, which can be sensed.

The frequency, amplitude, and/or phase of vibration of the electrode tip can be dampened by different amounts, depending on what type of object and/or medium the electrode tip $34^A$ contacts. For example, as discussed herein, when the electrode tip $34^A$ contacts tissue 13, a particular amount of energy can be imparted to the tissue 13 from the electrode tip $34^A$, thus dampening the vibration of the electrode tip $34^A$. The amount of energy imparted to the tissue 13, however, can be different than an amount of energy imparted to blood or another type of medium that the electrode tip $34^A$ contacts in route to a targeted site within the body. For example, a mechanical property (e.g., density) of air is different than a mechanical property of saline solution, which is different than a mechanical property of blood, which is different than a mechanical property of tissue 13. These different mechanical properties can lead to a different change in vibration of the electrode tip $34^A$, as the electrode tip $34^A$ comes into contact with different regions of a patient's vasculature and/or anatomy.

In some embodiments, when the electrode tip $34^A$ comes into contact with different types of objects and/or media (e.g., tissue 13, blood, saline solution, air), a change in vibration that occurs when crossing from one type of medium to the next may be reproducible. For example, when the electrode tip $34^A$ crosses an air-blood interface, blood-tissue interface, or air-tissue interface; for example, the vibration of the electrode tip $34^A$ may be reduced by a particular amount that is reproducible. Particular devices can be calibrated to factor in what type of interfaces (e.g., air-blood, blood-tissue, air-tissue) that the device will be operating in. As such, if in a particular procedure, the electrode assembly $11^A$ will be crossing a blood-tissue interface, the electrode assembly $11^A$ can be calibrated for this and can accurately correlate a dampening of the vibration to contact with the tissue 13. Alternatively, if in a particular procedure, the electrode assembly $11^A$ will be crossing an air-tissue interface, the electrode assembly $11^A$ can be appropriately calibrated for this and can accurately correlate a dampening of the vibration to contact with the tissue 13.

In some embodiments, the vibration element 32 can be configured to maintain the induced vibration after contact between the electrode $31^A$ and the object and/or medium. For example, the vibration element 32 can be configured to maintain a particular frequency, particular amplitude, and/or particular phase of the vibration inducing signal upon contact between the electrode $31^A$ and the object and/or medium. The particular frequency, particular amplitude, and/or particular phase can be maintained by varying an electrical drive signal of the vibration element 32. Increasing contact (e.g., magnitude of force) between the electrode $31^A$ and the object can result in changing (e.g., increasing) the electrical drive signal to maintain a substantially-steady-state vibration of the electrode $31^A$. The change to the electrical drive signal can be monitored with a sensor, for example, a current sensor.

The magnitude of change of the dampened frequency, amplitude, and/or phase of the vibration and/or change in electrical drive signal may be used to determine whether contact has occurred between the electrode tip $34^A$ and tissue 13. As used herein, contact can be defined as contact between the electrode tip $34^A$ and tissue 13, a magnitude of force applied between the electrode tip $34^A$ and tissue 13, and/or a vector of force applied to the electrode tip $34^A$ as a result of contact between the electrode tip $34^A$ and tissue 13. For example, in response to the frequency, amplitude, and/or phase changing by a defined amount, a determination that contact has occurred can be made (e.g., yes or no). Alternatively, the magnitude of change of the dampened frequency, amplitude, and/or phase of the vibration and/or the change in the electrical drive signal may be correlated to a magnitude of force applied between the electrode tip $34^A$ and tissue 13. As described more fully below, the vibration element 32 may be driven at any predetermined frequency, and not necessarily at a resonant frequency, where vibrations sensed by the second sensor may exhibit discernible differences in responsive vibration characteristics (e.g., frequency, amplitude, and/or phase) upon contact between the electrode $31^A$ and tissue 13, which can be analyzed to determine contact (e.g., whether contact has occurred, magnitude of force corresponding to contact).

In an example, as pressure is applied to the handle 21, increasing contact (e.g., magnitude of force) between the electrode tip $34^A$ and the tissue 13, vibrations produced by the vibration element 32 can be absorbed by the tissue 13. As such, the frequency, amplitude, and/or phase at which the electrode tip $34^A$ is vibrating, can be reduced. Alternatively, as pressure applied to the handle 21 is decreased, decreasing contact (e.g., magnitude of force) between the electrode tip $34^A$ and the tissue 13, vibrations can be less absorbed by the tissue 13. Therefore, the frequency, amplitude, and/or phase may be reduced less.

The electrode tip $34^A$ may be configured for axial movement $M_A$ and lateral movement $M_L$ relative to the electrode base $36^A$. A clearance gap 38 may exist between a portion of the electrode tip $34^A$ and the electrode base $36^A$ to accommodate any axial and lateral movements $M_A$, $M_L$ of the electrode tip $34^A$ relative to the electrode base $36^A$. The electrode base $36^A$ may be configured to securely connect to a distal end of the tubular body 22 of the catheter 19. A portion of the electrode base $36^A$ may be inserted into the tubular body 22.

Figure 5:
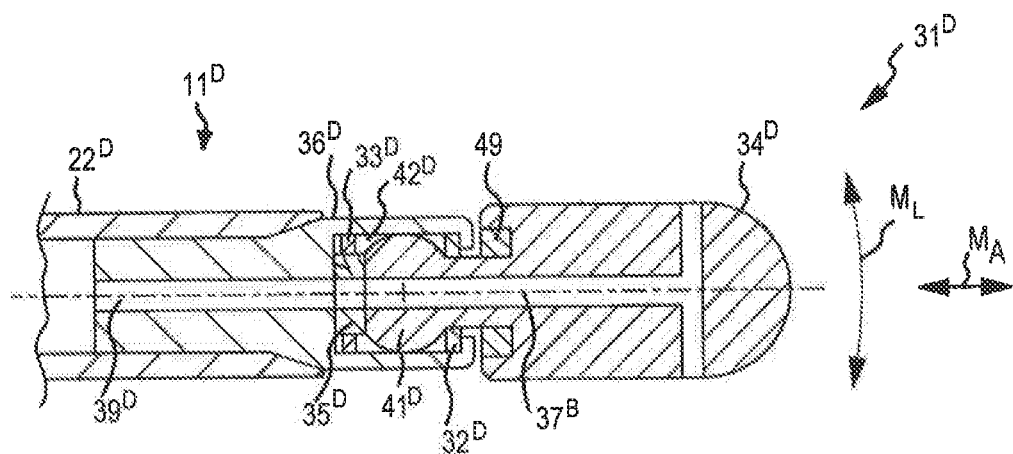
FIG. 5 is a cross-sectional view of another embodiment of the electrode assembly of the medical device of FIG. 1 configured to use vibration and deflection sensing to sense contact.

The electrode tip $34^A$ may also have a channel $37^A$ (or a plurality of channels as shown in FIG. 5) configured to allow a fluid to flow through or adjacent to the electrode tip $34^A$, such as for irrigation purposes. The electrode base $36^A$ may further include a channel 39 configured to allow a fluid to flow from a lumen in the tubular body 22, through the electrode base $36^A$, and to the electrode tip $34^A$, and may be used for irrigation purposes. The channel $37^A$ can line up with the channel 39 to some degree at all lateral movements of the electrode tip $34^A$ relative to the electrode base $36^A$.

Figure 3:
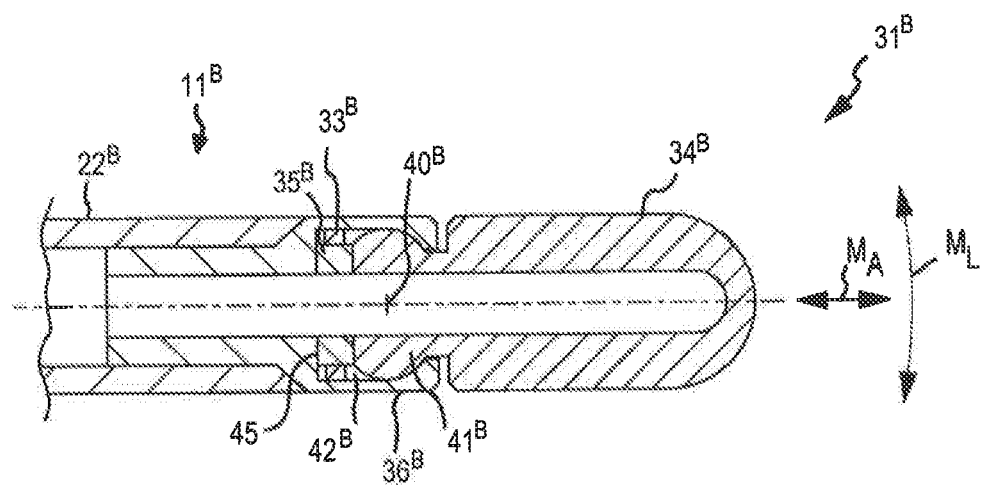
FIGS. 3 and 4 are cross-sectional views of other embodiments of the electrode assembly of the medical device of FIG. 1 configured to use deflection sensing to sense contact.

The electrode tip $34^A$ may be connected to the electrode base $36^A$ via a spherical joint $40^A$. The spherical joint $40^A$ may comprise a spherical knuckle $41^A$ located in a pocket $42^A$. The pocket $42^A$ may be substantially cylindrical in shape. In an embodiment, the knuckle $41^A$ may be a portion of the electrode base $36^A$ and the pocket $42^A$ may be a cavity located in the electrode tip $34^A$. In another embodiment (as generally illustrated in FIG. 3), the knuckle $41^A$ may be a portion of the electrode tip $34^A$ and the pocket $42^A$ may be a cavity located in the electrode base $36^A$.

The vibration element 32 may be configured to vibrate the electrode tip $34^A$ at a defined frequency, amplitude, and/or phase of vibration. The vibration element 32 may be fixedly or rigidly connected to the electrode tip $34^A$, such that vibrations produced by the vibration element 32 are transferred to the electrode tip $34^A$ via a contact point between the vibration element 32 and the electrode tip $34^A$. In some embodiments, the vibration element 32 may be located in the pocket $42^A$. The vibration element 32 may be annular and may be substantially similar in diameter to the pocket $42^A$. The vibration element 32 may include an aperture located in the center of the vibration element 32. The aperture may be used to allow fluid to pass through the vibration element 32. The aperture may be substantially the same diameter as the channel $37^A$ located in the electrode tip $34^A$. The vibration element 32 may be located in the pocket in the electrode tip $34^A$, at a distal position relative to the knuckle $41^A$. Alternatively, the vibration element 32 may be located in the pocket $42^A$ in the electrode base $36^A$, at a proximal position relative to the knuckle $41^A$ (as generally illustrated in FIG. 3). While a detailed embodiment of a vibration element is provided, it will be appreciated that this disclosure is not limited to the illustrated embodiments. Rather, other types and forms of vibration inducing transducers, including those known to those with skill in the art, may be used.

In embodiments, the second sensor may be configured to measure the frequency, amplitude, and/or phase of the vibration of the electrode tip $34^A$. When the electrode tip $34^A$ is not in contact with tissue 13, the second sensor may detect a frequency, amplitude, and/or phase substantially equal to a frequency (which may be predefined or predetermined), amplitude, and/or phase imparted to the electrode tip $34^A$ by the vibration element 32. When the electrode tip $34^A$ is in contact with tissue 13, the second sensor may detect changes in frequency, amplitude, and/or phase. The changes might be positive or negative depending on the specific design of the resonating structure, but the magnitude of the change will be proportional to a magnitude of force applied between the electrode tip $34^A$ and tissue 13.

In some examples, the second sensor can be annular in shape. The second sensor can be located on the electrode tip $34^A$; located distally with respect to the spherical knuckle $41^A$ in a pocket of the electrode tip $34^A$; or located proximally with respect to the spherical knuckle $41^B$ in the pocket of the electrode base $36^B$, as shown in FIG. 3.

In an embodiment, the system 10 may be programmed to determine whether contact between the electrode tip $34^A$ and tissue 13 has occurred. For example, a determination that contact has occurred between the electrode tip $34^A$ and the tissue 13 can be made in response to a differential between a first and second frequency, amplitude, and/or phase of vibration being exceeded. The first frequency, amplitude, and/or phase of vibration can be a frequency, amplitude, and/or phase that exists when the electrode tip $34^A$ is not in contact with tissue 13 and the second frequency, amplitude, and/or phase of vibration can be a frequency, amplitude, and/or phase that exists when the electrode tip $34^A$ is in contact with tissue 13. In some embodiments, the first and second frequency, amplitude, and/or phase can be correlated with a first and second magnitude of force applied between the electrode tip $34^A$ and tissue 13.

This allows the system 10 to be adjustable for determining the amount of force between the electrode tip $34^A$ and tissue 13 that must occur before the system acknowledges that contact with tissue 13 has occurred. For example, if the differential between the first and second frequency, amplitude, and/or phase of vibration is set high, then the magnitude of force applied between the electrode tip $34^A$ and tissue $13e$ to sufficiently determine that contact has been made may be high in magnitude. Additionally, if the differential between the first and second frequency, amplitude, and/or phase of vibration is set low, then the amount of contact force to sufficiently determine that contact has been made may be low in magnitude.

In some embodiments, the electrode assembly $11^A$ can include a deformable member $35^A$ and a deflection measuring sensor $33^A$, as further discussed in relation to FIG. 3. The deformable member $35^A$ and the deflection measuring sensor $33^A$ can be configured to measure a lateral displacement $M_L$ (e.g., angular) and axial displacement $M_A$ of the electrode tip $34^A$ relative to the electrode base $36^A$.

The deflection measuring sensor $33^A$ and/or the deformable member $35^A$ may be annular in shape and may be provided in the pocket $42^A$ in the electrode tip $34^A$. The deflection measuring sensor $33^A$ and/or the deformable member $35^A$ may be provided at a position distal to the knuckle $41^A$. In another embodiment (as generally illustrated in FIG. 3), the deflection measuring sensor $33^A$ and/or the deformable member $35^A$ may be located proximal to the knuckle 41 in the pocket $42^B$ in the electrode base $36^B$. In yet another embodiment, the deflection measuring sensor $33^A$ may be a piezoelectric transducer.

In some embodiments, the deflection measuring sensor $33^A$ and/or the second sensor may send a signal to the handle 21 and/or control unit 16, upon determining that contact has been made between the electrode tip $34^A$ and the tissue 13, or when the magnitude of force applied between the electrode tip $34^A$ and tissue 13 is greater than a defined amount. The signal to the handle 21 may be used to provide a required amount of haptic or visual feedback via the handle 21 (which may have been configured as previously described). The signal to the control unit 16 may be used to provide information to the user, such as through the various input/output devices 18a or the display 18b of the system 10.

As generally shown in FIG. 3, an embodiment of an electrode assembly $11^B$ may also be configured to measure lateral displacement $M_L$ (e.g., angular) and axial displacement $M_A$ of the electrode tip $34^B$ relative to an electrode base $36^B$. The magnitude of the displacements $M_L$, $M_A$ may be used to determine contact between the electrode tip $34^B$ and tissue 13, a magnitude of force applied between the electrode tip $34^B$ and tissue 13, and/or a vector of force applied to the electrode tip $34^B$ as a result of contact between the electrode tip $34^B$ and tissue 13. In an embodiment, the electrode assembly $11^B$ may comprise the electrode $31^B$ having the electrode tip $34^B$ and the electrode base $36^B$, a deformable member $35^B$, and a deflection measuring sensor $33^A$.

The deformable member $35^B$ is configured to deform when a force is applied between the electrode tip $34^B$ and tissue 13. The deformable member $35^B$ may be located adjacent to a flat portion of the knuckle $42^B$. As the electrode tip $34^B$ makes contact with tissue 13, the electrode tip $34^B$ will move relative to the electrode base $36^B$. Depending on the angle at which the electrode tip $34^B$ contacts the tissue 13, the electrode tip $34^B$ may move either axially $M_A$ and/or laterally $M_L$ relative to the electrode base $36^B$. When the electrode tip $34^B$ moves axially $M_A$ and/or laterally $M_L$ by pivoting about the spherical joint $40^B$, the deformable member $35^B$ may be squeezed against the flat portion of the knuckle $41^B$ and a rigid surface, such as a wall 45 of the electrode base $36^B$ (as shown in FIG. 3) or a surface of the vibration element 32 (as shown in FIG. 2). In some embodiments, the deformable member $35^B$ can expand radially outward. When the electrode tip $34^B$ is no longer in contact with tissue 13, the deformable member $35^B$ can elastically return to its initial form. The deformable member $35^B$ may be annular in shape and may have an aperture located at the center of the deformable member $35^B$ which may allow fluid to pass through the deformable member $35^B$. The deformable member $35^B$ may be provided or positioned in the pocket $42^B$ of the electrode tip $34^B$ between the knuckle $41^B$ and the electrode base $36^B$.

In another embodiment, shown in FIG. 3, the deformable member $35^B$ may be provided or positioned in the pocket $42^B$ of the electrode base $42^B$ between the knuckle $41^B$ and the wall 45 of the electrode base $36^B$. The amount of force necessary to deform the deformable member $35^B$ may be set or determined based on a selection of a material used for the deformable member $35^B$. For example, as the selected material of the deformable member $35^B$ becomes stiffer and more difficult to deform, the amount of force necessary to deflect the electrode tip $34^B$ may also increase. This may be useful, for example, in setting or determining the range of forces to be measured. In embodiments, the deformable member $35^B$ may comprise silicon, rubber, or other natural and manmade elastomeric materials. A wide variety of other elastically deformable materials may be used as known to those with skill in the art.

The deflection measuring sensor $33^B$ may be configured to measure the deformation of the member $35^B$. As the deformable member deforms (e.g., expands radially), the deflection measuring sensor $33^B$ may detect the deformation of the deformable member $35^B$. The deflection measuring sensor $33^B$ may be located on the deformable member $35^B$ and may be coaxial with the deformable member $35^B$ and surround the deformable member $35^B$. The deflection measuring sensor $33^B$ may be annular in shape. In an embodiment, the deflection measuring sensor $33^B$ may be a piezoelectric transducer configured for measuring strain. The magnitude of deformation of the deformable member $35^B$ detected by the deflection measuring sensor $33^B$ may correlate to a vector of force applied to the electrode tip $34^B$ as a result of contact between the electrode tip $34^B$ and tissue 13. The deflection measuring sensor $33^B$ may send a signal to the handle 21 and/or the control unit 16. The signal to the handle 21 may be used to provide a set or required amount of haptic or visual feedback for which the handle 21 may be configured to produce. The signal to the control unit 16 may be used to provide information to a user, such as through the various input/output devices 18a or the display 18b of the system 10.

Figure 4:
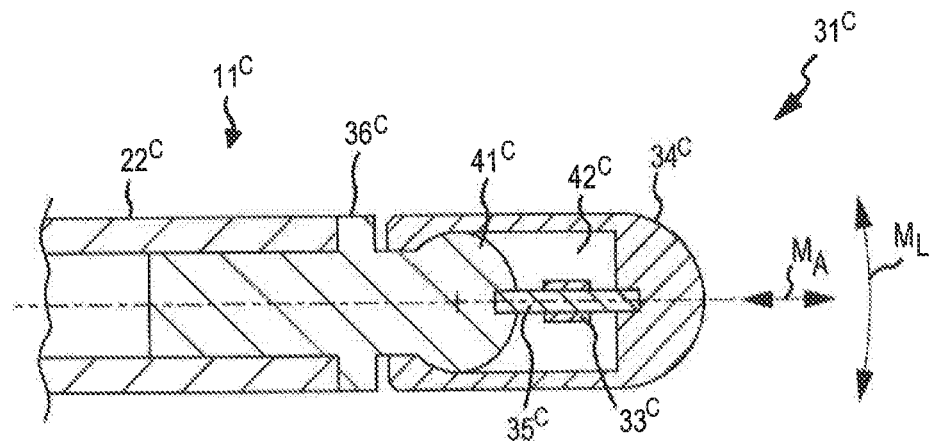

The deformable member $35^C$ may have various shapes. For example, as generally illustrated in FIG. 4, the deformable member $35^C$ may be a beam that is generally linear shaped, such as substantially cylindrical shaped or substantially rectangular shaped. The deformable member $35^C$ may be provided or positioned distally of the knuckle $41^C$ and provided or positioned in the pocket $42^C$. One end of the deformable member $35^C$ may be connected to the knuckle $41^C$ and the opposing end of the member may be connected to the electrode tip $34^C$. The deformable member $35^C$ can be longitudinally arranged along a longitudinal centerline of the catheter 19, extending from a distal end of the knuckle $41^C$ to a distal end of the pocket $42^C$. The electrode tip $34^C$ can be deflected axially $M_A$ or laterally $M_L$, causing deformation of the deformable member $35^C$. The deflection measuring sensor $33^C$, provided or positioned on deformable member $35^C$ may measure the deformation of the deformable member $35^C$.

In an embodiment, and as generally illustrated in FIG. 5, an electrode assembly $11^D$ may comprise an electrode $31^D$ having an electrode tip $34^D$ and an electrode base $36^D$, a deformable member $35^D$, a deflection measuring sensor $33^D$, a vibration element $32^D$ and a vibration measuring sensor 49.

The electrode assembly $11^D$ may be configured to determine contact between the electrode tip $34^D$ and tissue 13, a magnitude of force applied between the electrode tip $34^D$ and tissue 13, and/or a vector of force applied to the electrode tip $34^D$ as a result of contact between the electrode tip $34^D$ and tissue 13 by both vibration dampening sensing of the electrode tip $34^D$ and strain deflection measurements of the deformable member $35^D$, such as generally described with reference to FIGS. 2 and 3. By using both vibration dampening sensing of the electrode tip $34^D$ and strain deflection measurements of the deformable member $35^D$, the accuracy and/or range of measurements associated with determining contact between the electrode tip $34^D$ and tissue 13, magnitude of force applied between the electrode tip $34^D$ and tissue 13, and/or the vector of force applied between the electrode tip $34^D$ and tissue 13 may be increased. For example, the vibration measuring sensor 49 may be configured to measure small magnitudes of force applied between the electrode tip $34^D$ and tissue 13, while the deflection measuring sensor $33^D$ may be configured to measure larger magnitudes of force applied between the electrode tip $34^D$ and tissue 13. The vibration measuring sensor 49 may be provided or positioned directly on the electrode tip $34^D$. The deflection measuring sensor $33^D$ may be located directly on the deformable member $35^D$.

Figure 6:
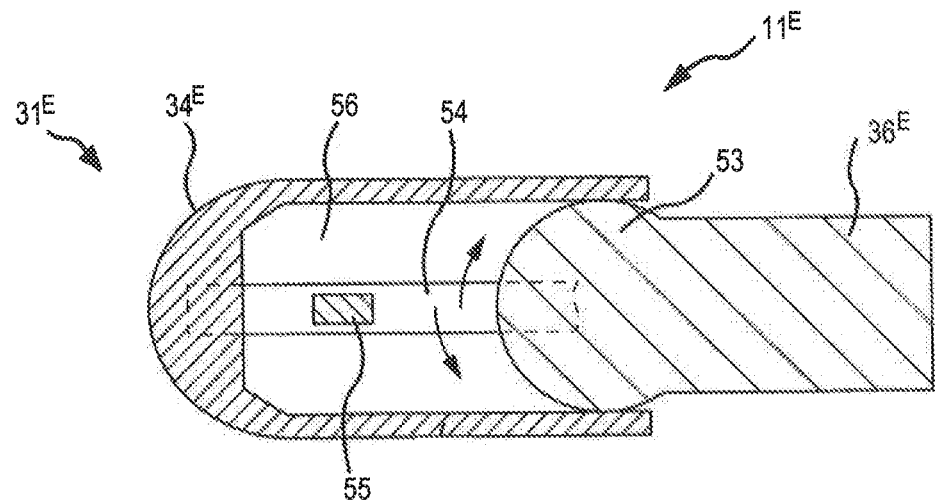

In yet another embodiment illustrated in FIG. 6, an electrode assembly $11^E$ may comprise electrode $31^E$ having an electrode tip $34^E$ and an electrode base $36^E$. The electrode assembly $11^E$ may further comprise a spherical joint 53, a beam 54 positioned distally of the spherical joint 53, one or more strain gauges 55 and a cavity 56. As shown, one end of the beam 54 may be connected to the spherical joint 53 and the other end of the beam 54 may be connected to the electrode $31^E$ at or near the electrode tip $34^E$.

The electrode assembly $11^E$ may be configured to measure contact between the electrode tip $34^E$ and tissue 13, a magnitude of force applied between the electrode tip $34^E$ and tissue 13, and/or a vector of force applied to the electrode tip $34^E$ as a result of contact between the electrode tip 34 and tissue 13 since any applied force on the electrode tip $34^E$ causes deflection in the beam 54, which generates feedback through the one or more strain gauges 55. Based on this embodiment, a determination can be made whether the force applied between the electrode tip $34^E$ and the tissue 13 is an axial force or a lateral force. Further, the one or more strain gauges 55 may be replaced with piezoelectric transducers, or other sensors to determine the contact between the electrode tip $34^E$ and tissue 13, the magnitude of force applied between the electrode tip $34^E$ and tissue 13, and/or the vector of force applied to the electrode tip $34^E$ as a result of contact between the electrode tip $34^E$ and tissue 13.

Figure 7:
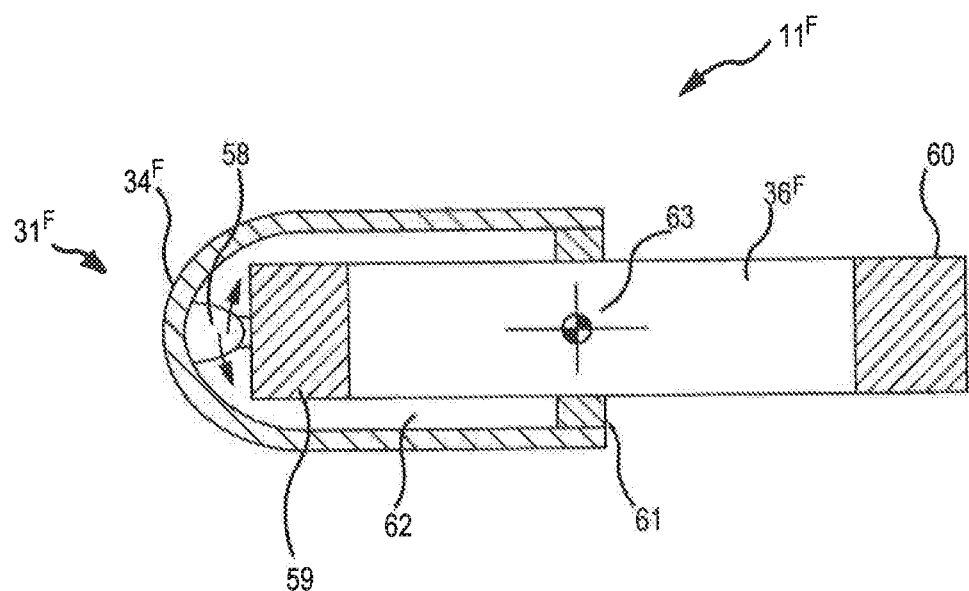

In yet another embodiment illustrated in FIG. 7, an electrode assembly $11^F$ may comprise electrode $31^F$ having an electrode tip $34^F$, an electrode base $36^F$, a standoff 58, a first piezoelectric transducer 59, a second piezoelectric transducer 60, a seal 61, and a cavity 62. The electrode tip 34$^F$ can move laterally with respect to the electrode base 36$^F$ at a center of rotation 63. The electrode 31$^F$ is connected to the electrode base 36$^F$ at the standoff 58 and the seal 61, such that when a force is applied to the electrode tip 34$^F$, either an axial force or a lateral force, the standoff impinges on the first piezoelectric transducer 59.

In operation, the second piezoelectric transducer 60 is electrically driven at a known frequency and the first piezoelectric transducer 59 is set up to recognize the output of the second piezoelectric transducer 60. When the electrode tip 34$^F$ is in contact with the tissue 13, the response output of the first piezoelectric transducer 59 will change with the applied load or tone of the tissue as a lesion is developed. The output of the first piezoelectric transducer 59 may be used to provide a signal for audible, visual, tactile, and/or other feedback to the user as described above. In some embodiments, the first piezoelectric transducer 59 can be configured to recognize an output of the second piezoelectric transducer 60. The output recognized by the first piezoelectric transducer 59 can be correlated to the magnitude of the contact force applied to the electrode tip 34$^F$. Further, the second piezoelectric transducer 60 may be optional and the first piezoelectric transducer 59 may be replaced with a strain gauge.

Figure 8:
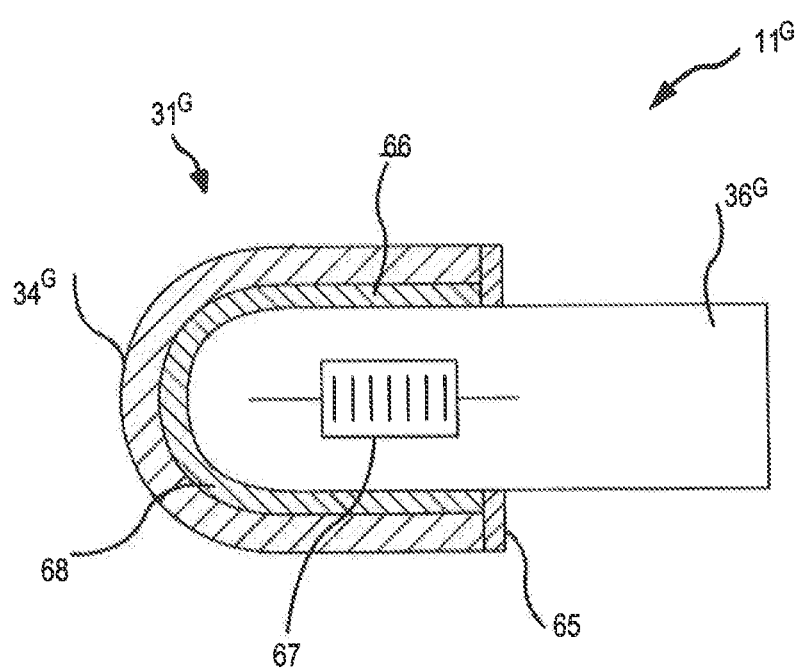

In yet another embodiment, illustrated in FIG. 8, an electrode assembly 11$^G$ may comprise electrode 31$^G$ having an electrode tip 34$^G$, and an electrode base 36$^G$, a seal 65, a fluid or gel 66, a strain gauge 67, and a cavity 68. The space between the electrode tip 34$^G$ and the electrode base 36$^G$ is filled with the fluid 66, which is retained in the cavity 68 by the seal 65. The fluid 66 has significant electrical resistance or impedance such that the closer the electrode tip 34$^G$ comes to the electrode base 36$^G$, the lower the resistance. Depending on where contact occurs between the electrode tip 34$^G$ and the tissue 13, a distance between the electrode tip 34$^G$ and the electrode base 36$^G$ can decrease, thus reducing the amount of fluid 66 and electrical resistance or impedance between a particular point of the electrode tip 34$^G$ and the base. A number of sensors (e.g., current sensors) can be placed on the electrode base 36$^G$, which can detect changes in current resultant from the varying distance between the electrode tip 34$^G$ and the electrode base 36$^G$. The detected changes in current can be correlated with measurements of contact between the electrode tip 34$^G$ and tissue 13, a magnitude of force applied between the electrode tip 34$^G$ and tissue 13, and/or a vector of force applied to the electrode tip 34$^G$. As discussed herein, the measurement can be based on capacitance and/or impedance associated with the fluid 66.

Further, the strain gauge 67 may measure the force on the electrode base 36$^G$ (or on the electrode tip 34$^G$) as the distance or thickness of space between the electrode tip 34$^G$ and the electrode base 36$^G$ changes. A number of strain gauges 67 can be placed on the electrode base 36$^G$ in the cavity 68. In an example, as force is applied to the electrode tip 34$^G$, a pressure in the cavity 68 can increase and can be registered by one of the number of strain gauges 67 and correlated with a magnitude of force and/or a vector of force applied to the electrode tip 34$^G$. Depending on where the force is applied to the electrode tip 34$^G$, one strain gauge 67 may register a greater pressure increase than another, providing for omni-directional measurement of force on the electrode tip 34$^G$.

As described above, when the electrode tip 34$^G$ is in contact with the tissue 13, the response output will change with the applied load or tone of the tissue as a lesion is developed. As with the embodiments described herein, the principles can be used for measuring changes in tissue tone as a means for assessing lesion development. Given that the mechanical characteristics of the tissue changes during and following RF ablation, the described embodiments could also be used to monitor the extent (e.g., size) of a lesion by recognizing changes in the feedback thru the transducers, strain gauges, or the like.

In yet another embodiment illustrated in FIG. 9A, an electrode assembly 11$^H$ may comprise electrode 31$^H$ having an electrode tip 34$^H$ and an electrode base 36$^H$. Similar to the embodiments shown in FIGS. 3 and 5, a knuckle 72 is incorporated along with a gap 73$^A$ between the electrode tip 34$^H$ and the electrode base 36$^H$. As further shown in FIG. 9B, a strain gauge 74 is located in the gap 73$^B$ between the electrode tip 34$^I$ and the electrode base 36$^I$. Lateral movement of the electrode tip 34$^I$ relative to the base 36$^I$ can change a size of the gap 73$^B$, which can be registered by the strain gauge 74. In some embodiments, multiple strain gauges 74 can be located in the gap 73$^B$ in a radial configuration. For example, strain gauges 74 can be located in one of three places, each 120° from each other, as shown in the layout in FIG. 9C. Other configurations using more or fewer than three transducers may be utilized with similar results. As described herein, the strain gauges 74 may be replaced with piezoelectric transducers, or various other types of sensors MEMS, LVDT, optical, laser, etc., configured to measure an increase or decrease in a size of the gap 73$^B$. Upon contact between the electrode tip 34$^H$ and the tissue 13, the strain gauges 74 (or transducers) will provide a signal for audible, visual, tactile and/or other feedback to the user as described above.

In yet another embodiment illustrated in FIG. 10, an electrode assembly 11$^J$ may comprise electrode 31$^J$ having an electrode tip 34$^J$, and an electrode base 36$^J$. The electrode tip 34$^J$ can have a first diameter and can be connected to a beam 81 of a second diameter at a proximal end of the electrode tip 34$^J$. The electrode base 36$^J$ includes an opening of a varying diameter passing from a proximal end to a distal end of the electrode base 36$^J$. The diameter of the opening at the distal end of the electrode base 34$^J$ can be smaller than the first diameter of the electrode tip 34$^J$ and larger than the second diameter of the beam 81. The beam 81 can be inserted into the opening of the distal end of the electrode base 36$^J$.

The electrode assembly 11$^J$ further comprises a transducer 78, which can be annular in shape, a compliant or deformable member 79, and a tensioned assembly 80. The tensioned assembly may be made up of the beam 81, similar to the beam in FIG. 6 and a band 82 stretched between the beam 81 and an end piece 83. The transducer 78 may be of any type of transducer that can sense a change in tension in the band 82, such as a strain gauge, piezoelectric, MEMS, LVDT, optical, laser, etc. Upon contact between the electrode tip 34$^J$ (or the electrode 31$^J$) and the tissue 13, the deformable member 79 can deform causing the tensioned assembly 80 to increase or decrease the amount of tension on the band 82. The transducer 78 will sense the change in tension and provide an output signal 84 for audible, visual, tactile and/or other feedback to the user as described above. For example, an increase or decrease in the amount of tension on the band 82 can pull the end piece 83 towards a distal end of the electrode tip 34$^J$, causing the end piece 82 to exert an increase or decrease in amount of force applied to the transducer 78. The transducer 78 can sense the increase or decrease in the amount of force applied on the transducer 78 and/or can sense the change in tension in the band 82, which can be used to determine contact between the electrode tip 34$^J$ and tissue 13, a magnitude of force applied between the electrode tip 34$^J$ and tissue 13, and/or a vector of force applied to the electrode tip 34$^J$.

Figure 11A:
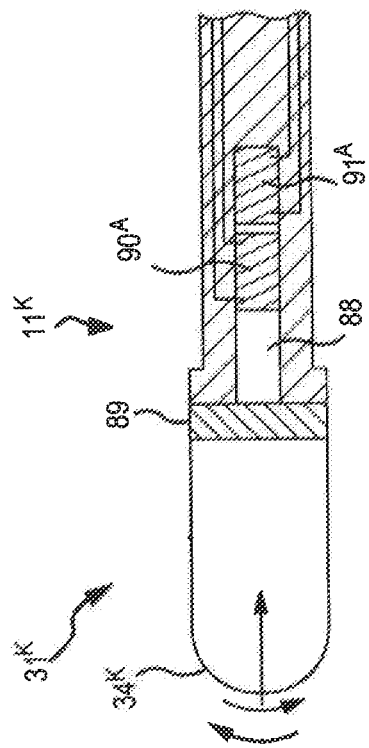

In yet another embodiment illustrated in FIG. 11A, an electrode assembly 11$^K$ may comprise electrode 31$^K$ having an electrode tip 34$^K$ of a first diameter, and an electrode shaft 88 of a second diameter. Electrode assembly 11$^K$ may further comprise a compliant or soft material 89, such as silicone, a piezoelectric receiver transducer 90$^A$, and a piezoelectric transmitter transducer 91$^A$. The electrode shaft 88 can be connected to the electrode tip 34$^K$. In addition, the piezoelectric receiver transducer 90$^A$ can be attached to a proximal end of the electrode shaft 88. The electrode shaft 88 and the piezoelectric receiver transducer 90$^A$ can be inserted into an opening at a distal end of an electrode base 94. In an example, the diameter of the opening at the distal end of the electrode base 94 can be smaller than the first diameter of the electrode tip 34$^K$ and larger than the second diameter of the electrode shaft 88.

An application of force to the electrode tip 34$^K$ can move the electrode tip 34$^K$, the electrode shaft 88, and the piezoelectric receiver transducer 90$^A$ proximally towards the piezoelectric transmitter transducer 91$^A$, such that the transducers contact one another, creating a signal which can be correlated with the application of force to the electrode tip 34$^K$.

Figure 11B:
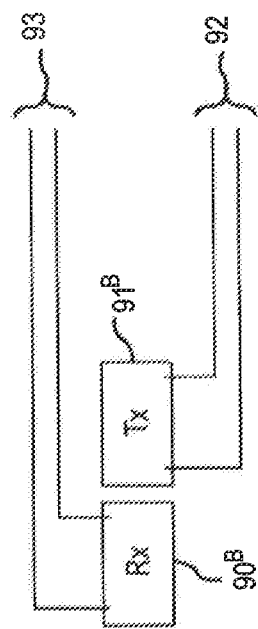
Figure 11C:
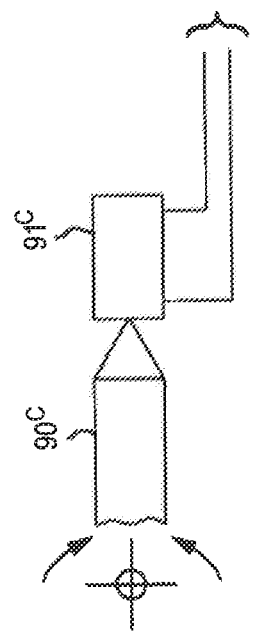
Figure 11D:
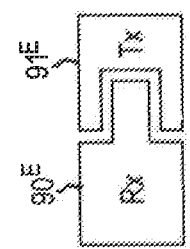

The piezoelectric receiver transducer 90$^B$ and piezoelectric transmitter transducer 91$^B$ are represented schematically in FIG. 11B along with the connections for the signal into the transmitter 92 and the signal out from the receiver 93. Additional embodiments are shown in FIG. 11C (indicating a pressure amplification due to a small contact area) and FIG. 11D (alternative transducer arrangements). For example, as the piezoelectric receiver transducer 90$^C$ moves towards and contacts the piezoelectric transmitter transducer 91$^C$, the piezoelectric receiver transducer 90$^C$ can contact the piezoelectric transmitter transducer 91$^C$ with a reduced contact area, leading to a pressure amplification between the point of the piezoelectric receiver transducer 90$^C$ and the piezoelectric transmitter transducer 91$^C$. The pressure amplification between the piezoelectric receiver transducer 90$^C$ and the piezoelectric transmitter transducer 91$^C$ can provide an increase in sensitivity. In some embodiments, the piezoelectric receiver transducer 90$^D$ can have a female contact face and the piezoelectric transmitter transducer 91$^D$ can have a male contact face. Alternatively, the piezoelectric receiver transducer 90$^E$ can have a female contact face and the piezoelectric transmitter transducer 91$^E$ can have a male contact face. In an example, the alternative transducer configurations in FIG. 11D can provide for a different sensitivities. As also described herein, the piezoelectric transducers 90$^A$, 91$^A$ may be replaced with strain gauges, MEMS microphones, LVDT, optical, laser, etc. Upon contact between the electrode tip 34$^K$ and the tissue 13, the electrode shaft 88 will move accordingly, such movement will be picked-up by the transducers, which will generate a signal as described above.

Figure 12:
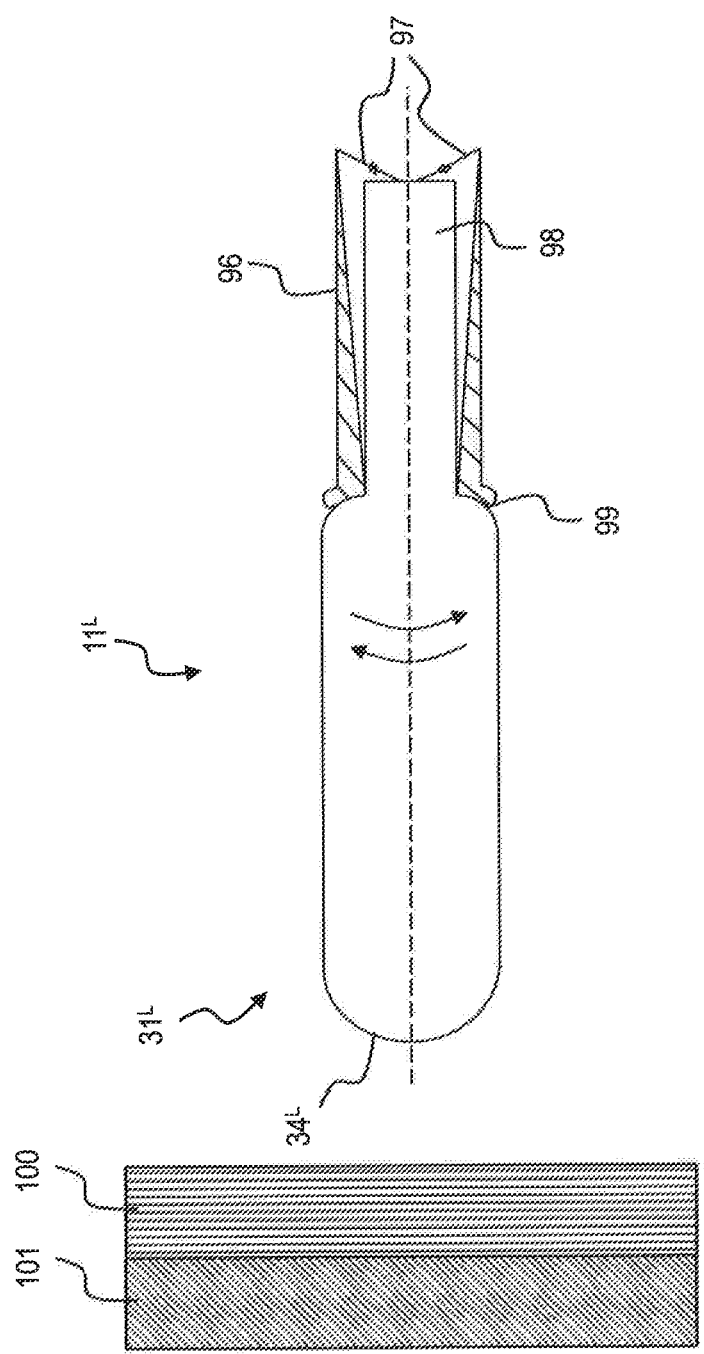

In yet another embodiment illustrated in FIG. 12, an electrode assembly 11$^L$ can include an electrode 31$^L$ having an electrode tip 34$^L$, an electrode base 96, a beam 98, swivel joint 99, and strain gauges 97. The electrode 31$^L$ can be connected to the beam 98 at a proximal end of the electrode 31$^L$. The beam 98 can extend through a portion of a length of the electrode base 96. In some embodiments, the electrode base 98 can be cylindrical and can have tapered inner walls, such that a distal opening of the electrode base 96 is substantially the same size as the beam 98 and a proximal opening of the electrode base 96 is larger than the distal opening. This can allow for movement of the beam 98 when deflection of the electrode tip 34$^L$ occurs. The electrode base 96 can be in contact with the electrode 31$^L$ via a swivel joint 99. Movement of the beam 98 can be detected by strain gauges 97 in contact with the beam 98 and the electrode base 96. For example, lateral movement of the electrode tip 34$^L$ caused by contact with tissue 13 can also cause movement of the beam 98, which can be detected by sensors 97. An output of the sensors 97 can be used to determine contact between the electrode tip 34$^L$ and tissue 101, a magnitude of force applied between the electrode tip 34$^L$ and tissue 101, and/or a vector of force applied to the electrode tip 34$^L$.

As discussed herein, the amount of energy imparted to the tissue 101 can be different than an amount of energy imparted to medium 100 (e.g., blood) that the electrode tip 34$^L$ contacts in route to a targeted site within the body. In an example, the electrode tip 34$^L$ can penetrate medium 100 to contact tissue 101. Mechanical properties of the tissue 101 and medium 100 can lead to a different change in vibration of the electrode tip 34$^L$, as the electrode tip 34$^L$ comes into contact with different regions of a patient's vasculature. Accordingly, the electrode assembly 11$^L$ can be calibrated to account for different types of media that the electrode tip 34$^L$ will contact, as discussed in relation to FIG. 2.

Various embodiments are described herein to various apparatuses, systems, and/or methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," or "an embodiment," or the like, means that a particular feature, structure, or characteristic described in connection with the embodiment is included in at least one embodiment. Thus, appearances of the phrases "in various embodiments," "in some embodiments," "in one embodiment," or "in an embodiment," or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features, structures, or characteristics of one or more other embodiments without limitation given that such combination is not illogical or non-functional.

It will be appreciated that the terms "proximal" and "distal" may be used throughout the specification with reference to a clinician manipulating one end of a medical device or instrument used to treat a patient. The term "proximal" refers to the portion of the device closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, medical devices may be used in many orientations and positions, and these terms are not intended to be limiting or absolute.

Although only certain embodiments have been described above with a certain degree of particularity, those skilled in the art could make numerous alterations to the disclosed embodiments without departing from the scope of this disclosure. Joinder references (e.g., attached, coupled, connected, and the like) are to be construed broadly and may include intermediate members between a connection of elements and relative movement between elements. As such, joinder references do not necessarily infer that two elements are directly connected/coupled and in fixed relation to each other. Additionally, the terms "electrically connected" and "in communication" are meant to be construed broadly to encompass both wired and wireless connections and communications. It is intended that all matter contained in the above description or shown in the accompanying drawings shall be interpreted as illustrative only and not limiting. Changes in detail or structure may be made without departing from the invention as defined in the appended claims.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A catheter comprising the following:
   an elongate tubular body comprising a distal end;
   a spherical joint comprising a joint proximal end and a joint distal end, the joint proximal end connected to the distal end of the elongate tubular body;
   a catheter tip connected to the joint distal end, wherein the spherical joint is configured to allow relative movement between the catheter tip and the elongate tubular body;
   a deformable member disposed adjacent to the spherical joint, wherein:
      the elongate tubular body, the catheter tip, the spherical joint, and the deformable member are configured to be inserted into a patient's body via the patient's vasculature; and
      movement of the spherical joint causes the deformable member to deform; and
   a deflection measuring sensor configured to measure a deformation of the deformable member.

2. The catheter of claim 1, wherein:
   the spherical joint includes a knuckle; and
   a deformable member is disposed adjacent to the knuckle.

3. The catheter of claim 2, further comprising a deflection measuring sensor configured to measure a deformation of the deformable member.

4. The catheter of claim 2, wherein a proximal end of the knuckle is connected to a distal end of a base and the base is connected to the distal end of the elongate tubular body.

5. The catheter of claim 4, wherein the deflection measuring sensor is configured to measure a magnitude of displacement between the catheter tip and the base.

6. The catheter of claim 5, wherein the magnitude of displacement between the catheter tip and the base is representative of a magnitude of force applied between the catheter tip and a tissue of a body.

7. The catheter of claim 5, wherein the magnitude of displacement between the catheter tip and the base is representative of a vector of force applied to the catheter tip.

8. The catheter of claim 1, wherein:
   the deformable member is configured to deform in response to a force being applied between the catheter tip and a tissue; and
   the elongate tubular body and the catheter tip are directly connected via the spherical joint.

9. The catheter of claim 8, wherein the deflection measuring sensor comprises a piezoelectric transducer.

10. The catheter of claim 1, wherein the deformable member is formed from an elastomeric material.

11. The catheter of claim 1, wherein:
    the spherical joint includes a knuckle connected to a distal end of the elongate tubular body; and
    the deformable member is disposed between the knuckle and the catheter tip.

12. A catheter comprising the following:
    an elongate tubular body comprising a distal end;
    a spherical joint comprising a joint proximal end and a joint distal end, the joint proximal end connected to the distal end of the elongate tubular body, wherein the spherical joint includes a knuckle;
    an electrode tip connected to the joint distal end, wherein the spherical joint is configured to allow rotational hinging between the electrode tip and the elongate tubular body; and
    a deformable member disposed between the knuckle and the electrode tip, the deformable member in contact with the knuckle and the electrode tip, wherein;
       the elongate tubular body, the catheter tip, the spherical joint, and the deformable member are configured to be inserted into a patient's body via the patient's vasculature; and
       movement of the spherical joint causes the deformable member to deform.

13. The catheter of claim 12, further comprising a deflection measuring sensor configured to measure a deformation of the deformable member, wherein the deflection measuring sensor is configured to measure a lateral displacement and axial displacement of the electrode tip.

14. The catheter of claim 13, wherein the deformable member is configured to deform when a force is applied between the electrode tip and a tissue.

15. The catheter of claim 13, wherein the elongate tubular body and the electrode tip are directly connected via the spherical joint.

16. An electrode assembly, comprising:
    an electrode tip configured to deliver energy to a tissue, the electrode tip being connected to a distal end of a catheter configured for insertion into a patient's body via the patient's vasculature;
    an electrode base slidingly coupled with the electrode tip;
    a first piezoelectric transducer connected with the electrode tip; and
    a second piezoelectric transducer coupled with the electrode base, wherein the electrode tip and the first piezoelectric transducer are configured to longitudinally slide towards the second piezoelectric transducer in response to an application of force to the electrode tip, wherein:

the piezoelectric transmitter transducer and the piezoelectric receiver transducer generate a signal in response to the application of force to the electrode tip, the signal representative of the application of force; and a force applied to the electrode tip is determined based on the signal representative of the application of force.

17. The electrode assembly of claim 13, wherein the first piezoelectric transducer is a receiver and the second piezoelectric transducer is a transmitter.

18. The electrode assembly of claim 17, wherein the piezoelectric transmitter transducer is held in fixed relation to the electrode base.

19. The electrode assembly of claim 13, wherein the piezoelectric receiver transducer and the piezoelectric transmitter transducer generate the signal as a result of contact between the piezoelectric receiver transducer and the piezoelectric transmitter transducer.

\* \* \* \* \*